United States Patent [19]

Melker et al.

[11] Patent Number: 5,135,492
[45] Date of Patent: Aug. 4, 1992

[54] ARTERIAL/VENOUS FLUID TRANSFER SYSTEM

[75] Inventors: Richard J. Melker; Gary J. Miller, both of Gainesville, Fla.

[73] Assignee: University of Florida, Gainesville, Fla.

[21] Appl. No.: 371,378

[22] Filed: Jun. 26, 1989

[51] Int. Cl.⁵ .......................................... A61M 31/00
[52] U.S. Cl. ........................................ 604/53; 604/86; 604/248
[58] Field of Search ................................ 604/51–53, 604/82, 83, 86–88, 244, 246, 248, 280, 283; 128/763

[56] References Cited

U.S. PATENT DOCUMENTS

| | | |
|---|---|---|
| 3,162,195 | 1/1962 | Dick . |
| 3,310,048 | 12/1963 | Ewing . |
| 3,502,097 | 6/1966 | Muller . |
| 3,613,663 | 9/1968 | Johnson . |
| 3,804,090 | 5/1972 | Holbrook . |
| 3,990,445 | 1/1975 | Lundquist . |
| 4,230,128 | 3/1978 | Aramayo . |
| 4,312,362 | 10/1980 | Kaufman . |
| 4,333,479 | 10/1979 | Shiplee . |
| 4,601,703 | 12/1984 | Herlitze . |
| 4,645,496 | 2/1987 | Oscarsson ........................... 604/248 |
| 4,759,756 | 7/1988 | Forman et al. ...................... 604/413 |
| 4,776,843 | 11/1980 | Martinez et al. . |
| 4,803,999 | 1/1988 | Liegner . |
| 4,834,716 | 5/1989 | Ogle, II ............................... 604/192 |
| 4,865,583 | 9/1989 | Tu ....................................... 604/53 |
| 4,908,018 | 3/1990 | Thomsen ............................ 604/83 |
| 4,934,375 | 6/1990 | Cole et al. .......................... 128/673 |
| 4,968,309 | 11/1990 | Andersson .......................... 604/283 |

FOREIGN PATENT DOCUMENTS

| | | | |
|---|---|---|---|
| 0111723 | 6/1984 | European Pat. Off. ............. | 604/86 |
| 3031242 | 8/1980 | Fed. Rep. of Germany . | |
| 2049513 | 3/1971 | France ................................. | 604/88 |

Primary Examiner—John D. Yasko
Assistant Examiner—Adam J. Cermak
Attorney, Agent, or Firm—Spensley Horn Jubas & Lubitz

[57] ABSTRACT

A fluid transfer system, including a channel member, adapted for connection between an arterial or venus catheter and an IV fluid administration system. The channel member includes a duct and an access port. An adapter including a recessed needle assembly is provided for mounting to the access port of the channel member. A syringe, IV tubing or an evacuated container may be mounted directly to the channel member via the adapter. Safety is substantially enhanced by recessing the needle assembly of the adapter.

4 Claims, 2 Drawing Sheets

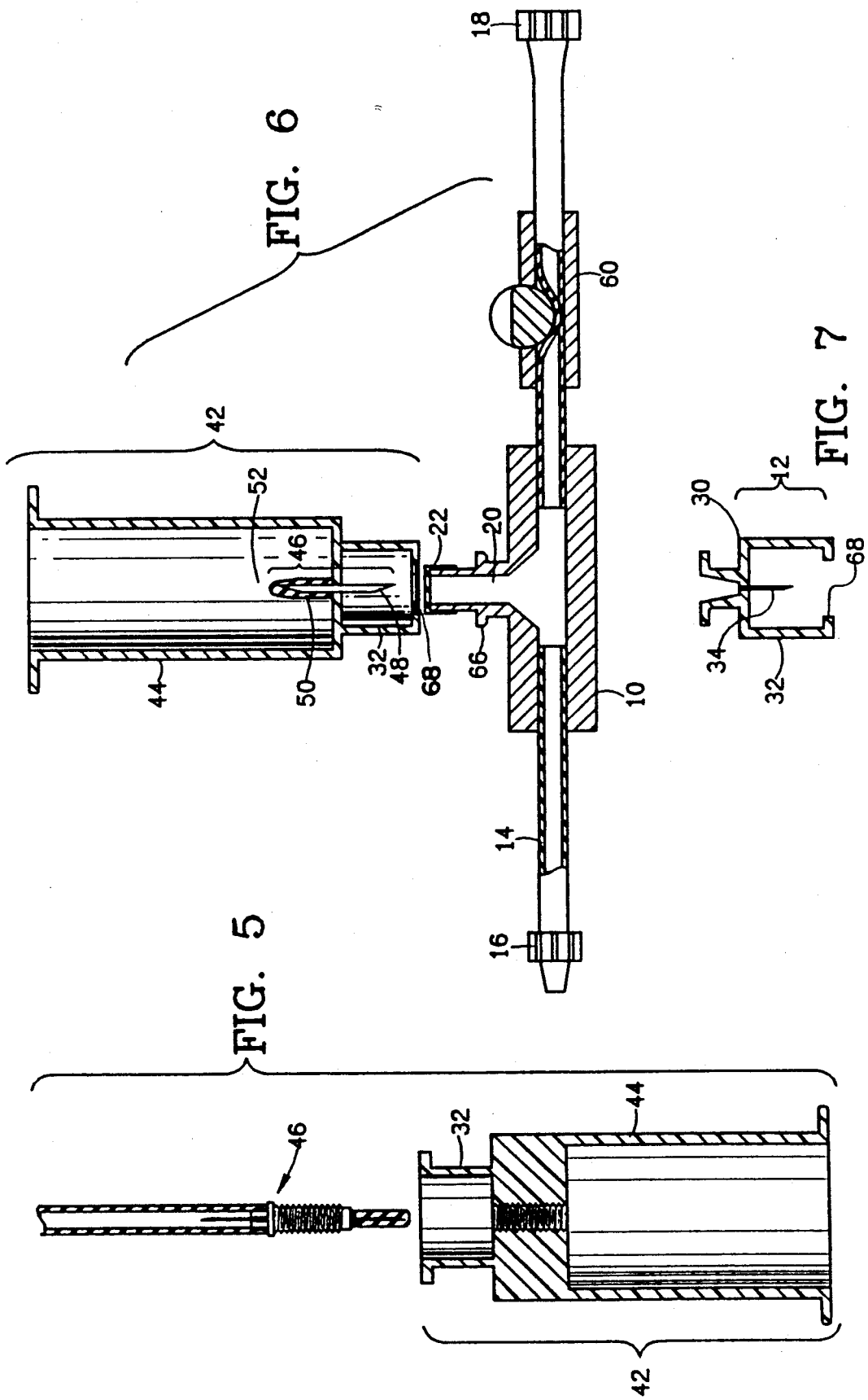

ARTERIAL/VENOUS FLUID TRANSFER SYSTEM

BACKGROUND OF THE INVENTION

1. Field of the Invention

This invention relates generally to medical devices for accessing a patient's circulatory system. More particularly, this invention relates to improved-safety assemblies used for withdrawing blood from and administering therapeutic fluids to a patient connected to intravenous or intraarterial lines.

2. Description of Related Art

It is common practice in hospitals to administer therapeutic fluids through or draw blood for laboratory studies from intravenous or intraarterial ("IV") lines connected to patients. This practice avoids the discomfort and risk a patient would experience from additional needle sticks required to directly access the patient's circulatory system.

Generally, IV lines are equipped with a multi-port stopcock. In typical practice, a blood sample is obtained by disrupting the flow of IV fluid to the patient through one port with a turn of the stopcock, attaching a syringe to a second port of the stopcock, withdrawing blood contaminated with IV fluid from the line, attaching a new syringe to the second port of the stopcock and, finally, drawing a sample. The initially drawn sample of blood contaminated with IV fluid may be reinjected or discarded. In any case, the first port of the stopcock is opened to the IV fluid supply and the IV line is then flushed with fluids.

A blood sample to be used for laboratory studies is typically transferred to an evacuated container by placing a hypodermic needle on the syringe and pushing the needle cannula through the rubber stopper of the evacuated container so that the blood is drawn into the container by the vacuum until the container is filled or the syringe is empty.

Unfortunately, this technique for drawing laboratory samples has several serious shortcomings. First, stopcocks are a common source of nosocomial infections since they become contaminated with blood and IV fluids during the withdrawal and reinfusion steps. Second, this method of transferring blood is costly since the equipment is relatively expensive and the intravenous tubing with stopcocks must be replaced frequently to minimize the occurrence of nosocomial infections. Third, and most important, this method of blood transfer requires extreme skill and care to avoid injury to hospital personnel. Specifically, needle stick injuries are likely to occur since the syringe must be equipped with a hypodermic needle and the hypodermic needle must then be guided toward an evacuated container held in the hand of hospital personnel. Needle sticks may also occur during recapping of the needles or later, during clean-up procedures.

Accidental needle sticks with blood contaminated needles represent a major health problem to hospitals, other medical facilities, and their personnel. It is estimated that there are 800,000 needle sticks per year in the United States resulting in a cost for testing and care of approximately $500,000,000. While needle sticks have been a problem since the invention of hypodermic needles, the recognition of the transfer of the AIDS virus by needle sticks has amplified concern over this problem. A number of other viral and bacterial infections (e.g., Hepatitis B, tuberculosis, and malaria) can also be transmitted by accidental needle stick injuries.

The same problems may occur when therapeutic fluids (for example, antibiotics, chemotherapeutics, and nutrients) are administered through IV lines. Therapeutic fluids may be administered to a patient connected to IV lines by equipping a syringe with a hypodermic needle, inserting the needle cannula into a container filled with the therapeutic fluid and drawing a desired amount, and then inserting the needle directly into the IV fluid container, or a piggyback container if present, through an injection port generally provided on these containers. Alternatively, the needle may be removed from the fluid containing syringe, the syringe attached to the stopcock and therapeutic fluid administered through it. Again, if extreme care is not taken with either method, needle stick injuries may occur during attachment of the hypodermic needle to the syringe, during the handling of the syringe equipped with the hypodermic needle, during removal of the needle from the syringe, during recapping of the needle, or during clean-up procedures.

Most research on the prevention of needle stick injuries has been directed towards developing safer needle caps. However, to date no solutions to the above-referenced multiple problems associated with blood and other fluid transfer have been disclosed.

SUMMARY OF THE INVENTION

The present invention provides a fluid transfer system which is safer for both patients and medical personnel. More specifically, the present invention reduces the risk of nosocomial infections to the patient by eliminating the need to draw and reinfuse fluids through a multi-port stopcock. The invention also reduces the risk of needle stick injury to medical personnel by providing a recessed needle arrangement and by drawing blood directly into an evacuated container during sampling.

The system of the present invention includes a channel member provided with a duct therethrough. One end of the duct is adapted to attach to a catheter implanted in a vein or artery of a patient. The other end of the duct is adapted to attach to an IV fluid administration system, i.e. IV tubing leading to an IV fluid container. The channeling member further includes a capped access port in flow communication with the duct. In the preferred embodiment, an integral valve is disposed within the duct at a location upstream of the access port, with reference to the direction of flow of fluid from the IV fluid container. The valve may be opened or closed to control fluid flow to the patient by manipulating a lever or similar control.

Additionally, the system includes an adapter provided with a mounting member which is mountable on the access port of the channel member. The adapter includes an integral housing and a recessed needle assembly. In one embodiment of the invention, the housing of the adapter is adapted to hold a syringe or IV tubing connected to a container containing therapeutic fluid ("therapeutic fluid set"). The needle assembly comprises one needle cannula recessed within the mounting member, in flow communication with the housing. Blood samples may be drawn into a syringe or therapeutic fluid may be administered from a syringe or the therapeutic fluid set as follows: The syringe or IV tubing is securely attached to the housing and thereby placed in flow communication with the needle cannula; the adapter with securely-held syringe or IV tubing is mounted to the channel member whereby the needle cannula pierces the cap of the access port and flow communication is established between the syringe or therapeutic fluid set and the patient's vein or artery via the duct and catheter.

In another embodiment of the invention, the housing is adapted to hold an evacuated container and the needle assembly comprises two needle cannulas in flow communication with one another. The first needle cannula is recessed within the mounting member. The second needle cannula is provided with a sheath and is recessed within the housing.

To draw a blood sample, the valve is closed, thereby halting the flow of IV fluid through the channel member. The adapter is mounted to the access port of the channel member, allowing the first needle cannula to pierce the cap of the access port, thereby establishing flow communication with the duct. An evacuated container is placed in the housing such that the sheath of the second needle is depressed and pierced by the second needle and the cap of the evacuated container is also pierced. Flow communication between the interior of the container and the patient's vein or artery is established via the duct and catheter and a sample of blood is thus drawn directly into the evacuated container.

With this inventive assembly, needle sticks are substantially prevented since the only needles present are safely recessed and it is unnecessary to separately equip a syringe with a hypodermic needle and aim an unprotected needle towards an evacuated container or a catheter access point.

The adapter of the invention may be disposable or, alternatively, may be multiuse with a removable, disposable needle assembly. Therefore, the patient's blood will only be exposed to sterile environments and nosocomial infections may be avoided. Use of an integral valve in lieu of a multi-port stopcock further reduces the risk of occurrence of nosocomial infections since the duct and its access port are easily flushed and are never open to the external environment.

BRIEF DESCRIPTION OF THE DRAWINGS

FIG. 5 is an enlarged cross-sectional side view of an adapter for holding evacuated containers wherein the needle assembly is removable.

FIG. 6 is a cross-sectional side view of an embodiment of the invention wherein the adapter snaps over or locks around the access port.

FIG. 7 is a cross-sectional side view of an adapter used for holding a syringe which may be used with the channel member depicted in FIG. 6.

Like reference characters in the various drawings refer to like elements.

DETAILED DESCRIPTION OF THE INVENTION

The following description is of the best presently contemplated mode of carrying out the invention. This description is made for the purpose of illustrating the general principles of the invention and should not be taken in a limiting sense. The scope of the invention is best determined by reference to the appended claims.

Figure 1:
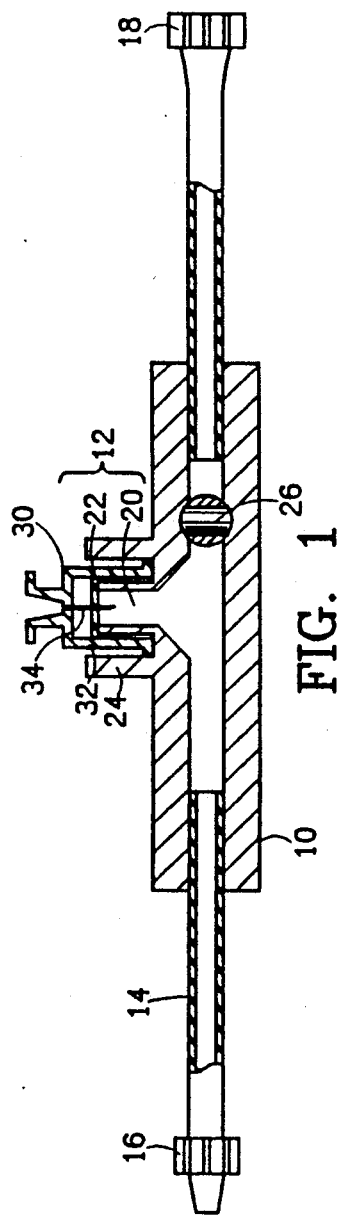
FIG. 1 is a cross-sectional side view of one embodiment of the invention wherein the adapter is configured to hold a syringe or IV tubing.
Figure 2:
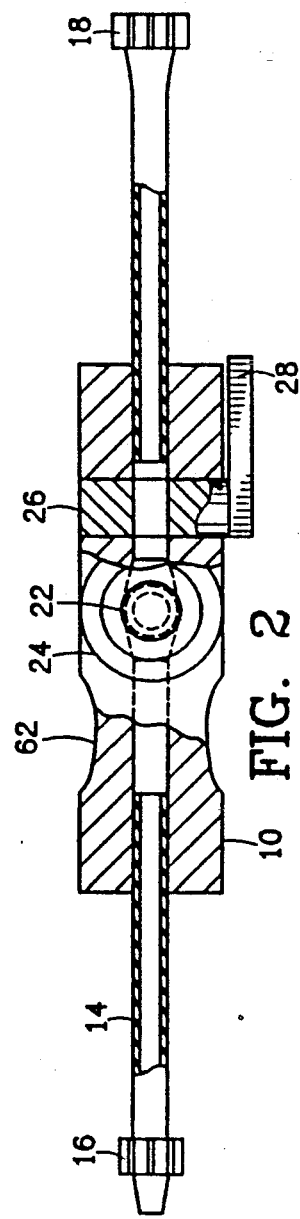
FIG. 2 is a top view of the channel member of the embodiment of the invention depicted in FIG. 1.

Referring now to the drawings, and initially to FIGS. 1 and 2, the preferred components of the inventive fluid transfer system can be seen. The system includes a channel member 10 and an adapter 12, both preferably made of a suitable, non-toxic plastic (for example, polytetrafluoroethylene plastic).

The channel member 10 is provided with a duct 14 and is adapted to connect to an IV fluid administration system. Specifically, one end of the duct 14 is adapted to connect to an arterial or venous catheter implanted in a patient. Typically, such catheters are equipped with a female Luer adapter for connecting to IV tubing. Therefore, to adapt one end of the duct for connection to a catheter, a male Luer adapter 16, as shown in FIG. 1, is preferably provided to securely connect the channel member 10 to the catheter. The other end of the duct is adapted to securely connect to IV tubing leading to an IV fluid container. Typically, IV tubing is provided with a male Luer adapter for mating to the female Luer adapters of the catheters. Therefore, the end of the duct 14 to be connected to the IV tubing is preferably provided with a female Luer adapter 18.

The channel member 10 further includes an access port 20 in flow communication with the duct 14. The access port is provided with a cap 22 preferably made of a resilient, self-sealing, non-toxic material (for example, a synthetic rubber). The access port is recessed within an open ended first mounting member 24. The first mounting member 24 preferably consists of the female portion of a bayonet mount (see FIGS. 1 and 4) or a snap-on mount (see FIG. 6). However, other coupling means may be used.

In the preferred embodiment, the channel member 10 comprises an integral valve 26 disposed within the duct, upstream of the access port 20 with reference to the direction of flow of IV fluid through the duct from an IV fluid container connected to the channel member 10. The valve 26 may be of any type which may be opened to allow fluid to pass and closed to prevent fluid from passing by manipulation of an external lever or actuator 28. Alternatively, a nonintegral valve or other flow-control device may be placed upstream of the channel member 10 to control the flow of fluid to the channel member 10. For example, flow-control devices which regulate or cut-off fluid flow in flexible tubing by controllably "squeezing" the tubing are known and could be used (e.g., clamps, such as clamp 60, depicted in FIG. 6).

The adapter 12 of the inventive assembly includes a housing 30 having a second mounting member 32. The housing 30 and second mounting member 32 are preferably a single unit. The second mounting member 32 is adapted to removably connect to the first mounting member 24 of the channel member 10. In the preferred embodiment, the second mounting member 32 consists of a male bayonet mount to mate with the female bayonet mount 24 of the channel member 10. The housing 30 is adapted to hold a syringe or IV tubing by removably locking either thereto. Standard syringes and IV tubing are typically provided with male Luer lock adapters. Thus, the housing 30 may, for example, be shaped into a female Luer lock adapter to which a standard syringe or IV tubing may be securely attached. The adapter 12 further comprises a needle assembly consisting of a single needle cannula 34 recessed within the mounting member 32.

The embodiment of the invention including the adapter depicted in FIG. 1 may be used to administer therapeutic fluids such as, for example, medication, to a patient having a catheter in place. This embodiment may also be used to withdraw fluid, for example, to withdraw blood contaminated with IV fluid prior to sampling using the adapter 42 depicted in FIG. 3.

The embodiment using the adapter 12 is used by mounting a syringe or IV tubing of the therapeutic fluid set into the housing 30. The valve 26 of the channel member 10 is then closed and the adapter 12 is mounted by connecting the second mounting member 32 to the first mounting member 24 of the channel member 10, whereby the recessed needle cannula 34 pierces the cap 22 of the access port 20. Flow communication is thus established between the syringe or therapeutic fluid set and the vein or artery of the patient via the duct 14. After the therapeutic fluid has been administered (or, when a syringe is used to withdraw fluid, after fluid has been withdrawn), the adapter 12 and syringe or IV tubing are removed and the integral valve 26 is opened to flush the duct. The syringe or IV tubing with adapter in place can then be discarded. Alternatively, the adapter 12 may then be removed from the syringe or IV tubing and discarded. If fluid was withdrawn using a syringe, the fluid contained in the syringe may later be readministered to the patient using a fresh adapter 12 or the fluid may be discarded. The channel member 10 and IV tubing of the therapeutic fluid set need not be replaced.

Figure 3:
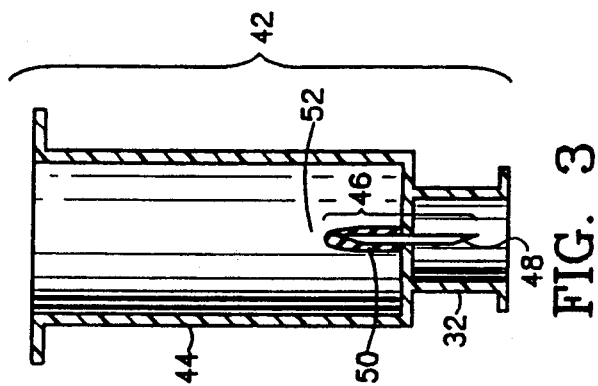
FIG. 3 is a side view of an adapter of another embodiment of the present invention used to hold an evacuated container for drawing biological fluid samples.

FIGS. 3 and 6 depict an alternate embodiment of an adapter 42 which may be mounted to the channel member 10. In this embodiment, the housing 44 of the adapter 42 consists of a cylindrical tube sized to hold an evacuated container such as, for example, a standard vacuum tube typically used in medical laboratories and again includes a second mounting member 32. The needle assembly 46 of the illustrated embodiment consists of two interconnected needle cannulas. A first needle cannula 48 is recessed within the second mounting member 32. The needle cannula 48 is of a length sufficient to pierce the cap 22 of the access port 20 when the adapter 42 is mounted to the channel member 10. A second needle cannula 50 in flow communication with the first needle cannula 48 is recessed within the housing 44. The second needle cannula 50 is provided with a sheath 52 made of a resilient, self-sealing, non-toxic material (e.g. a synthetic rubber).

The adapter 42 may be a single disposable unit or, alternatively, the needle assembly 46 may be removable, as depicted in FIG. 5, and the mounting member 32-housing 44 unit may be reused with a new needle assembly. Examples of suitable removable needle assemblies are the assemblies manufactured by Sherwood Medical, marketed under the trademark MONOJECT, and by Becton Dickinson marketed under the trademark VACUTAINER SYSTEM.

The inventive system, as described above, is a less expensive, safer method for drawing blood than the methods presently used, since only the needle assembly or adapter need be replaced and all needles are safely recessed. The channel member 10 and IV tubing need not be replaced.

The embodiment of the inventive assembly depicted in FIGS. 3 and 6 may be utilized to draw blood directly into an evacuated container, thus eliminating the dangerous intermediary steps of equipping a syringe into which a blood sample has been drawn with a hypodermic needle and guiding the needle towards an evacuated container held in the hand of medical personnel. Specifically, the assembly is used as follows:

The flow of IV fluid through the channel member 10 is disrupted by closing valve 26 (FIG. 1) or tightening clamp 60 (FIG. 6) and the adapter 42 is mounted to the channel member 10 by connecting the second mounting member 32 of the adapter 42 to the first mounting member 24 of the channel member 10. The first needle cannula 48 thereby pierces the cap 22 of the access port 20 and establishes flow communication with a vein or artery of the patient via the duct 14. The sheath 52 of the second needle cannula 50 prevents fluid from the duct from escaping into the housing 44. An evacuated container is then placed into the housing whereby the sheath 52 is depressed and pierced by the second needle cannula 50 which then immediately pierces the cap 22 of the evacuated container. Blood contaminated with IV fluid from the duct 14 is then drawn into the evacuated container by action of the vacuum therein. The evacuated container is removed and discarded and a fresh evacuated container is inserted into the housing 44 to draw the blood sample for evaluation. After the desired sample has been drawn, the evacuated container is removed from the adapter 42. The sheath 52 of the second needle cannula 50 expands to cover the needle cannula 50 and thereby prevents fluid from leaking from the adapter 42 after the evacuated container has been removed but while the adapter 42 is still mounted to the channel member 10. Next, the adapter 42 is removed from the channel member 10, allowing the cap 22 to again seal the access port 20. Finally, the valve 26 is opened or clamp 60 is loosened and the duct 14 is flushed with IV fluid.

Figure 4:
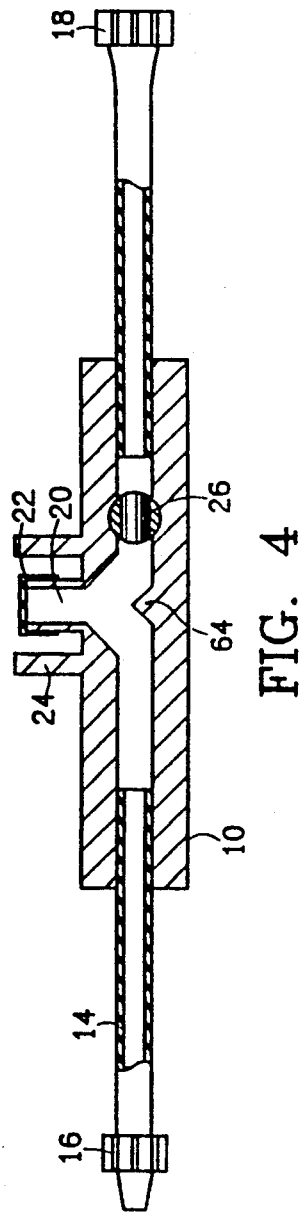
FIG. 4 is a cross-sectional side view of a channel member equipped with a flow diverter.

The channel member 10 of the present invention may additionally be provided with parallel indentations 62 which serve as finger grips, as shown in FIG. 2, to aid medical personnel in stabilizing the channel member 10 while mounting an adapter 12, 42 or transferring fluid. Furthermore, as depicted in FIG. 4, a flow diverter 64 may be provided inside the duct 14 in line with the access port 20 to create turbulence when IV flows through the duct 14. Adequate flushing of the access port 20 following a fluid transfer is thereby ensured.

FIGS. 6 and 7 depict an alternate technique for mounting adapters 12 or 42 to the channel member 10. In these embodiments, mounting member 32 of adapters 12 and 42 "snaps" over a flange 66 provided on the access port 20 of the channel member 10. Alternatively, flange 66 may form an incomplete ring (i.e. having two or more openings) and the adapters 12, 42 may be mounted to channel member 10 by inserting the wings 68 of the mounting members 32 into the openings of the flange 66. The adapter 12, 42 is then locked onto the channel member with a slight twist.

The inventive fluid transfer system, as described above, provides a cost-efficient method of reducing the risk of needle stick injuries to medical personnel involved with transferring fluids to and from the veins or arteries of patients by providing a novel recessed needle assembly. The inventive system furthermore provides a cost-efficient method of reducing the risk of nosocomial infections to patients by eliminating the need for drawing fluids through a multi-port stopcock and by shielding fluid entering the patient from the external environment.

Several preferred embodiments of the present invention have been described. However, it will be understood that various modifications may be made without departing from the spirit and scope of the invention. For example, the various elements can be made of different materials and in different general shapes. Accordingly, it is to be understood that the invention is not to be limited by the specific illustrated embodiments, but only by the scope of the appended claims.

We claim:

1. A method for administering therapeutic fluids to a patient also requiring intravascular (IV) fluid, comprising the steps of:
   (a) implanting a vascular catheter into the vascular system of a patient;
   (b) providing an IV fluid administration system;
   (c) providing a channel member comprising a duct having first and second ends, the first end being adapted to connect to an intravascular catheter, the second end being adapted to attach to an IV fluid administration system, the channel member further comprising an access port in flow communication with the duct;
   (d) connecting the first end of the duct to the catheter implanted in the patient's vascular system and connecting the second end of the duct to the IV fluid administration system;
   (e) channeling IV fluid from the IV fluid administration system to the catheter through the duct of the channel member;
   (f) providing a syringe;
   (g) providing an adapter comprising a mounting member adapted to connect to the access port of the channel member, a housing shaped to secure the syringe thereto, and a needle assembly recessed within the mounting member;
   (h) drawing therapeutic fluid to be administered to the patient into the syringe;
   (i) securing the syringe to the housing of the adapter whereby flow communication is established between the syringe and the needle assembly;
   (j) stopping the IV fluid from flowing through the channel member;
   (k) then establishing flow communication between the recessed needle assembly of the adapter and the channel member by mounting the mounting member of the adapter to the access port of the channel member; and
   (l) thereafter administering the medication from the syringe to the patient by channeling the therapeutic fluid through the needle assembly, into the duct of the channel member and from there to the catheter implanted in the vascular system of the patient.

2. The method of claim 1 wherein the channel member further comprises an integral valve disposed within the duct at a location upstream of the access port with reference to the direction of flow of IV fluid from the IV fluid administration system, whereby IV fluid is stopped from flowing through the channel member when the valve is closed.

3. A system for transferring fluids to and from a patient's circulatory system through a vascular catheter comprising:
   (a) a channel member comprising:
      (i) a duct extending therethrough, the duct having first and second ends, the first end being adapted to attach to a vascular catheter, the second end being adapted to attach to an intravascular (IV) fluid administration system;
      (ii) an access port in flow communication with the duct, the access port being provided with a self-sealing cap and being recessed within a first mounting member;
   (b) an adapter, comprising:
      (i) a second mounting member for removably mounting the adapter to the access port, wherein the second mounting member is adapted to mate with the first mounting member;
      (ii) a housing connected to the second mounting member; and
      (iii) a needle assembly comprising a first needle cannula, recessed within the second mounting member, a first end of the first needle cannula being in flow communication with the housing, whereby when the adapter is mounted to the access port of the channel member, a second end of the first needle cannula pierces the cap of the access port and is placed in flow communication with the access port; and
   (c) a flow diverter disposed inside the channel member duct in line with the access port whereby, when fluid channels through the channel member duct, turbulence is created and the access port is flushed.

4. The fluid transfer system of claim 3, wherein the channel member further includes an integral manually closable valve disposed within the duct at a location upstream of the access port with reference to the direction of flow of IV fluid through the channel member.

* * * * *